United States Patent [19]
Wright et al.

[11] Patent Number: 5,147,538
[45] Date of Patent: Sep. 15, 1992

[54] FIELD-PORTABLE APPARATUS AND METHOD FOR ANALYTICAL SUPERCRITICAL FLUID EXTRACTION OF SORBENT MATERIALS

[75] Inventors: Bob W. Wright; Jonathan S. Fruchter, both of Richland, Wash.

[73] Assignee: Electric Power Research Institute, Inc., Palo Alto, Calif.

[21] Appl. No.: 790,190

[22] Filed: Nov. 8, 1991

Related U.S. Application Data

[62] Division of Ser. No. 510,987, Apr. 19, 1990, Pat. No. 5,087,360.

[51] Int. Cl.$^5$ ............................................. B01D 15/08
[52] U.S. Cl. ................................. 210/198.2; 210/181; 210/541; 210/634; 210/656; 210/659; 55/386; 422/70
[58] Field of Search ............... 210/541, 635, 656, 659, 210/198.2, 181, 634; 422/70, 261; 55/386

[56] References Cited

PUBLICATIONS

B. W. Wright, C. W. Wright, R. W. Gale, and R. D. Smith, "Analytical Supercritical Fluid Extraction of Adsorbent Materials," *Anal. Chem.*, 59 (1987) 38–44.

K. Sugiyama, M. Saito, T. Hondo, and M. Senda, "New Double Stage Separation Analysis Method: Directly Coupled Laboratory-Scale Supercritical Fluid Extraction-Supercritical Fluid Chromatography, Monitored with a Multiwavelength Ultraviolet Detector," *J. Chromatogr.*, 332 (1985) 107–116.

S. B. Hawthorne and D. J. Miller, "Extraction of Recovery of Organic Pollutants from Environmental Solids and Tenax-GC Using Supercritical $CO_2$," *J. Chromatogr. Sci.*, 24 (1986) 258–64.

S. B. Hawthorne and D. J. Miller, "Extraction and Recovery of Polycyclic Aromatic Hydrocarbons from Environmental Solids Using Supercritical Fluids," *Anal. Chem.*, 59 (1987) 1705–1708.

M. M. Schantz and S. N. Chestler, "Supercritical fluid extraction procedure for the removal of trace organic species from solid samples," *J. Chromatogr.*, 363 (1986) 397–401.

B. W. Wright, C. W. Wright, and J. S. Fruchter, "Supercritical Fluid Extraction of Coal Tar Contaminated Soil Samples," *Energy & Fuels*, 3 (1989) 474.

Lee, M. L. et al., "Retention Indices for Programmed-Temperature Capillary-Column Gas Chromatography of Polycyclic Aromatic Hydrocarbons," *Anal. Chem.*, 51, No. 6 (May 1979).

Vassilaros, D. L., et al., "Linear Retention Index System for Polycyclic Aromatic Compounds, Critical Evaluation and Additional Indices," *J. Chromat.* 252 (1982) 1–20.

Czubryt, J. J. et al., "Solubility Phenomena in Dense Carbon Dioxide Gas in the Range 270–1900 Atmospheres," *J. Phys. Chem.*, 74, No. 24 (1970).

Wise, S. A. et al., "Determination of Polycyclic Aromatic Hydrocarbons in a Coal Tar Standard Reference Material," *Anal. Chem.* (1988), 60, 887–894.

Villaume, J. F., "Coal Tar Wastes: Their Environmental Fate and Effects," Hazardous and Toxic Wastes: Technology, Management and Health Effects, Majumdar, S. K., Miller, E. W., (1984) The Pennsylvania Academy of Science (pp. 362–375).

*Primary Examiner*—Ernest G. Therkorn
*Attorney, Agent, or Firm*—Limbach & Limbach

[57] ABSTRACT

A field-portable supercritical fluid extraction apparatus uses an SFE solvent delivery means, SFE solvent cooling means, and reciprocating high pressure liquid chromatography pump having a cooled pumphead. A solid matrix sample is contained within an extraction cell. The SFE solvent is preheated in the extraction cell oven before it is introduced into the extraction cell. After contact with the solid matrix the extraction effluent passes through a heated restriction tube before passing into a collection flask assembly having a collection solvent tube and a collection solvent condenser to condense collection solvent vapors entrained by escaping SFE solvent. The analytes are collected in the collection solvent. The SFE solvent cooling means, pumphead and collection solvent condenser are all cooled by the combination of a single stage thermoelectric device, liquid-cooled heat exchanger and convective heat sink.

1 Claim, 7 Drawing Sheets

FIELD-PORTABLE APPARATUS AND METHOD FOR ANALYTICAL SUPERCRITICAL FLUID EXTRACTION OF SORBENT MATERIALS

This is a divisional of application Ser. No. 07/510,987, filed Apr. 19, 1990, U.S. Pat. No. 5,087,360.

TECHNICAL FIELD

This invention relates generally to the use of supercritical fluid extraction to extract semivolatile and higher molecular weight materials from solid sorbent matrices, and more particularly, this invention relates to a field-portable apparatus for providing supercritical fluid extraction solvent to sorbent materials at supercritical conditions, and collecting the extracted analytes in a collection solvent.

BACKGROUND OF THE INVENTION

Prior to widespread availability of natural gas, gas for fuel and light was manufactured by the hightemperature carbonization of bituminous coal, resulting in a product called "town gas" or "manufactured gas". These early gasification activities, which date back to the 1800s, resulted in the formation of coal tar residues. These residues were usually either burned on site as a supplemental fuel or land-disposed of near the plant. Villaume, J.F. *Hazardous and Toxic Wastes: Technology, Management and Health Effects;* Majumdar, S.K., Miller, E.W., Eds.; The Pennsylvania Academy of Science: Philadelphia, PA, 1984: pp 362-375. As a result of such practices, abandoned town gasification sites or disposal sites are now becoming recognized as environmental trouble spots. Due to the widespread use of town gas in the late 19th and early 20th century, there are expected to be many such sites around the country. Consequently, it is necessary to have reliable methods for the analysis of soil samples that could potentially be contaminated with varying quantities of coal tar or other organic wastes.

Most current methods for the measurement of organics in soils and sediments require lengthy solvent extraction. In order to implement remedial measures and to carry out cost-effective site assessments, more rapid and field-adaptable sample extraction methods are desirable. Supercritical fluid extraction (SFE) techniques provide a viable alternative with promising advantages over the current liquid extraction methods. Wright, G.W.; Wright, C.W.; Gale, R.W.; Smith, R.D. *Anal. Chem.* 1987, 59, 38-44. Schantz, M.M.; Chesler, S.N. *J. Chromatoor.* 1986, 363, 397-401. Hawthorne, S.B.; Miller, D.J. *Anal. Chem.* 1987, 59, 1705-1708.

While the SFE technique was originally applied to the analysis of coal tar waste, it is applicable to any type of semivolatile organic compounds that contaminate solid materials. For examples, it has been applied to petroleum tars and PCBs from fly ashed, bottom ashed, sediment, and sludges.

The potential advantages of SFE accrue from the properties of a solvent at temperatures and pressures above its critical point. The liquidlike solvating power and rapid mass-transfer properties of a supercritical fluid provide the potential for more rapid extraction rates and more efficient extraction due to better penetration of the matrix than is feasible with liquids. The properties of a supercritical fluid are intermediate between those of the gas and those of the liquid phases. The compressibility of a supercritical fluid is large just above the critical temperature, and small changes in pressure result in large changes in the density of the fluid. The density of a supercritical fluid is typically $10^2$–$10^3$ times greater than that of the gas. Molecular interactions increase at these higher densities because of shorter intermolecular distances, and solvating characteristics of the supercritical fluid approach those of a liquid. However, the diffusion coefficients and viscosity of the fluid remain intermediate between those of the gas and liquid phases, thus allowing rapid mass transfer of solutes compared to a liquid. The properties of a supercritical fluid are dependent on the fluid composition, pressure, and temperature. Many fluids have comparatively low critical temperatures that allow extractions to be conducted at relatively mild temperatures. For example, the critical temperature of carbon dioxide is only 31° C. Density or solvating power of a supercritical fluid can be controlled by fluid pressure and/or temperature. In addition, various different fluids or fluid mixtures that exhibit different specific chemical interactions can be used to obtain the desired solvent strength and selectivity.

Although the basis and primary advantage of supercritical fluid extraction is derived from fundamental physical properties, specific instrument design criteria are necessary to fully exploit its potential, particularly for field applications. The present invention was designed specifically for field applications where portability, extraction speed, ease of operation, minimal requirements for ancillary supplies, and samples analysis flexibility (e.g., ability to be analyzed by a variety of analytical approaches) are more significant factors than in laboratory applications. Consistent with this philosophy, the apparatus was designed for use with carbon dioxide, but other pressurized liquids or ambient pressure liquids could also be utilized. The field-portable SFE apparatus of the present invention provides the following operation characteristics:

1. Sample sizes ranging from a few milligrams to several grams (5) can generally be quantitatively extracted in less than thirty minutes. The present device is designed to extract solids (as opposed to liquids) with particles ranging up to 3-4 mm in diameter. Alternative extraction cells could be designed to allow extraction of liquid samples.

2. Wet samples (e.g., containing water) can be extracted directly. It is not necessary to dry a sample before placing it in the extraction cell. The properties of supercritical carbon dioxide and th design of the system allows the water to be removed during extraction and collected (as a separate phase) with the analytes.

3. Rapid extraction is possible due to relatively fast flow rates of the supercritical fluid. Fresh fluid is continuously purged through the sample matrix and depressurized into a collection flask to trap the analytes. Liquid flow rates of several mL ($\leq 10$) per minute at pressures over 600 bar can be delivered by the pumping system. The maximum operating pressure is limited by the specific extraction cell design. Typical cells allow operation up to 450 bar and cells with "quickconnects" are presently limited to pressures up to 300 bar. Since a reciprocating pump is used, nearly unlimited fluid volumes can be continuously utilized. The pumping system allows control of the fluid pressure (solvating power) enabling selective extraction or fractionation of analytes with different fluid phase solubilities.

4. Extractions can be conducted at temperatures ranging from essentially ambient (although the critical temperature of carbon dioxide is 31° C.) to over 250° C. If extraction cells are used containing polymer seals, it may be necessary to use lower temperatures. Choice of operating temperature is dependent on the nature of the analytes and the matrix. For thermally stable analytes, a high operating temperature may allow more efficient desorption from an adsorptive matrix. For carbon dioxide, maximum operating temperatures of 100°-150° C. are typical. The fluid is preheated prior to entering the extraction cell to provide more homogeneous solvating power through the extraction matrix.

5. Provisions are provided to heat the extraction effluent to higher than the extraction temperature ($\leqq 400°$ C.) just prior to analyte collection. The fluid is depressurized by expansion through a restrictor orifice and considerable JouleThomson cooling occurs, particularly at the fast fluid flow rates needed for rapid extraction of larger size samples. This cooling can freeze the orifice closed (with carbon dioxide and/or water) or allow it to become plugged with analytes unless extra heat is added to the system. The actual flow rate of the fluid is governed by the diameter of the restrictor tubing which can range from 50-100 $\mu$m i.d.

6. The analytes are collected by bubbling the extraction effluent through an appropriate organic solvent (methylene chloride, etc.) as the fluid is expanded. Studies have shown that near quantitative loss of analytes to the atmosphere can occur through aerosol formation unless the aerosol is disrupted (1). Bubbling the expanded gas through a solvent is a convenient way of disrupting the aerosol. Expansion of a fluid to a gas results in a volume increase of approximately 1000 fold. Consequently, gas flows of over several liters per minute are bubbled through the solvent. To prevent sample and solvent loss, the collection system was designed to efficiently contain the solvent and minimize evaporation. Only 10-20 mL of solvent are needed for each sample. Thus, expensive solvent consumption and lengthy solvent concentration procedures are minimized. A variety of analytical determination methods can then be used for subsequent sample analysis.

7. The apparatus is designed to extract a single sample at a time, but it has tandem sample processing capabilities. This allows near continuous extraction of sequential samples since one sample can be connected or removed from the apparatus while the other one is being extracted.

8. Many of the components of the extraction system are self-cleaning or can be recycled with minimal cleaning. Spent extraction cells are free of extractable organics and can be rinsed with water and air dried.

9. Carbon dioxide cylinders provide a convenient mechanism of supplying a high-purity and non-toxic extraction solvent in the field. Depending on the sample matrix, approximately 5 to 10 samples can be extracted with 1 pound of carbon dioxide. Small aluminum cylinders are available that weigh approximately 50 lbs. and contain 20 lbs. of carbon dioxide. This would service between 100 and 200 extractions.

SUMMARY OF THE INVENTION

The field-portable supercritical fluid extraction ("SFE") apparatus of the present invention utilizes an SFE solvent delivery systems, ordinarily a pressurized cylinder or tank, which delivers SFE solvent to a cooling unit comprising a copper block cooled by a first thermoelectric cooler assembly. A reciprocating high pressure liquid chromatography pump is provided having a pumphead onto which is fastened a copper plate and then a second thermoelectric cooler assembly. Pressurized SFE solvent is then passed through coiled tubing contained within an extraction cell oven before it passes into the extraction cell containing the solid sorbent matrix sample. The resulting extraction effluent, containing any desorbed analytes, is depressurized in a heated restriction tube which is sealingly received within a collection flask assembly. This collection flask assembly has a collection tube for holding collection solvent and a collection solvent condenser to condense collection solvent vapors entrained by SFE solvent leaving the collection flask assembly. The thermoelectric cooler assemblies are characterized by the combination of a wafer-shaped, single stage thermoelectric cooler, liquid cooled copper heat exchanger and a convective cooled heat sink.

BRIEF DESCRIPTION OF THE FIGURES

FIG. 6 is a side elevational view of the collection vessel assembly, with detailed views of the condenser assembly and cooling channel, FIGS. 6a and 6b, respectively.

DETAILED DESCRIPTION OF THE INVENTION

Figure 1:
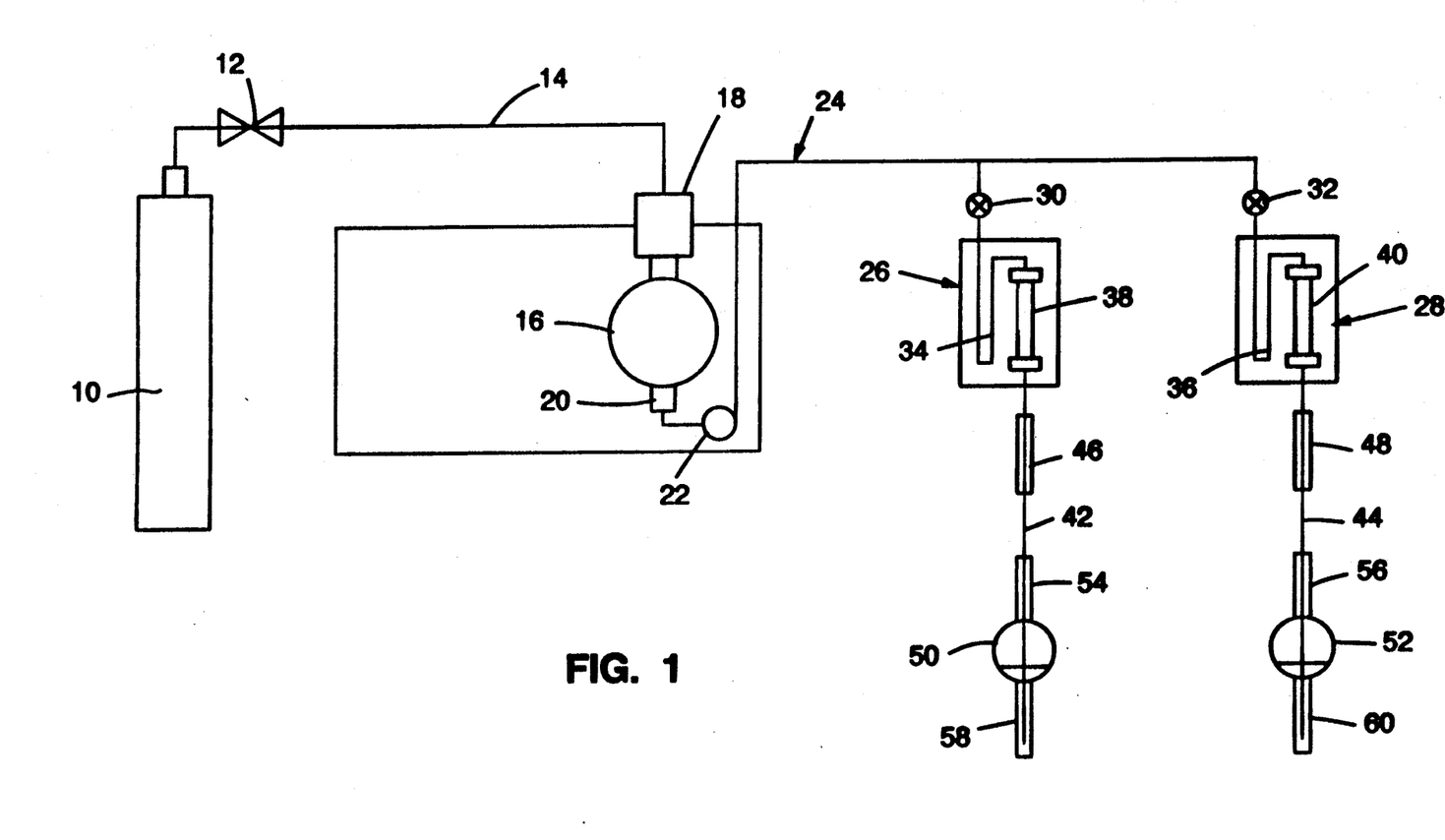
FIG. 1 is a schematic diagram of the fieldportable extraction apparatus of the present invention.

FIG. 1 shows a schematic diagram of the preferred embodiment of the field-portable SFE apparatus. The actual instrument (not shown here) which has been constructed according to a preferred embodiment of this invention measures approximately fourteen inches wide by fourteen inches high by thirteen inches deep and weighs approximately twenty-five kilograms. The extraction ovens and restrictor heaters are mounted on the top of the instrument and the collection vessels are mounted vertically on the right side of the instrument to permit easy manipulation of the extraction cells.

Referring to FIG. 1, SFE solvent supply 10 is a pressurized cylinder whose size is selected according to the portability required and the commercial availability of the SFE solvent containers. We have used small aluminum cylinders containing twenty pounds of carbon dioxide, weighing about fifty pounds total, capable of performing between one hundred and two hundred extractions. A shut-off valve 12 is provided to isolate the SFE solvent supply 10 from the remainder of the system.

In the preferred embodiment of the invention, carbon dioxide is used as the SFE solvent. There are, however, other SFE solvents which may be used. Preferably, polar organic solvent characterized by lower critical temperatures. This group would include methanol, isopropanol, acetonitrile, and other solvents which provide the appropriate chemical interaction with sorbent matrix and analytes. In on particularly preferred embodiment, a mixture of carbon dioxide and methanol is used as the SFE solvent. Obviously, those of ordinary skill in the art will appreciate that other solvents and other solvent delivery systems can be used and still practice the present invention.

Tube 14 (⅛" OD, stainless steel) connects SFE solvent supply 10 to a commercially available reciprocating high pressure liquid chromatography pump 16 to furnish a high pressure fluid supply. Rabbit HPX pump (Rainin Instruments, Woburn, MA) was the only commercially available device that met the requisite flow and pressure specifications for the subject invention. A pressure control module (not shown in FIG. 1) from Rainin Instruments is also provided in the preferred embodiment. This pressure control module was removed from its case and mounted inside the electronic module of the Rabbit HPX pump. To allow convenient placement of the digital pressure display and the other pressure controls, the pump flow controls were mounted on the back panel of the pump. The pumphead attachment bracket was modified to allow the pumphead to be rotated 180° so the inlet port was pointing up rather than down.

In order to pump the SFE solvent with a reciprocating pump 16, and to prevent vapor locking, we found it advantageous to cool both the incoming SFE solvent and the pumphead. Our experience with carbon dioxide as the SFE solvent shows that temperatures between 0° and 9° C. are adequate. SFE solvent cooling assembly 18 provides cooling to the incoming SFE solvent. A complete description of SFE solvent cooling assembly 18 is found below, with particular reference made to the elements shown in FIG. 3. High pressure pump 16 has a pumphead which is adapted to receive a pumphead cooling assembly 20 to prevent vapor lock. Assembly 20 is more completely described below with reference to FIG. 2.

Pressure transducer 22 is provided in the pump effluent to assist in the control of the pump 16. Pressurized SFE solvent is pumped through tube 24 (1/16" OD, stainless steel) to the pre-selected extraction oven 26 or 28. The pressurized solvent is directed to the proper extraction oven by opening and closing the on/off valves 30 and 32 associated with each extraction oven. Inside the extraction ovens 26 and 28 are found several meters of tightly coiled tube 34 and 36 respectively, which serve to preheat the SFE solvent prior to its entry into extraction cells 38 and 40. In our preferred embodiment, the extraction cell ovens 26 and 28 are custom cylindrical heating mantles (five inches by one and one-half inch ID, 115 volts, 80 watts, Glass Col., Terra Haute, IN) which are powered by a miniature microprocessor temperature controller (CN9000, Omega, Stamford, CT).

Extraction cells 38 and 40 are used to contact the solid sorbent matrix to which analytes may be bound with SFE solvent, under supercritical conditions. Several types of extraction cells may be used. We use all stainless steel components for high temperature operation, i.e. over 125° C. These cells are constructed from one to four inch lengths of ¼" ID stainless steel tubing capped with Swagelok stainless steel zero-volume ¼" to 1/16" column end fittings (SS-400-6-1ZV) containing 1.0 μm pore size sintered stainless steel frits. These devices must be tightened with wrenches and are prone to leak after multiple uses (greater than five). Another, more convenient type of extraction cell uses a polymer seal around the frits, but is limited to operation at temperatures less than 125° C. These lower temperature cells are available commercially from Keystone Scientific (Bellefonte, PA) in lengths ranging from 1 to 12 cm. having 4.6 mm ID. The internal diameter of the extraction cells must be kept narrow ($\leq 5/16"$) to prevent flow channeling through the matrix with subsequent inefficient and unreliable extraction. The fluid supply line 24 could be connected to the extraction cell with a "quick-connect" if pressures lower than 300 bar are used. Higher pressure operation requires typical high pressure fittings.

Extraction effluent from the extraction cells 38 and 40 is depressurized in heated restrictors 42 and 44. In the preferred embodiment, restrictors 42 and 44 are 100 μm i.d. fused silica or stainless steel capillary tubing. Lower flow rates can obviously be obtained with smaller restrictor tubing. The restrictor tubing is routed through a 2 mm i.d.×3 in. ceramic tube furnaces 46 and 48 to provide additional heat to the extraction effluent if required. The tube furnaces 46 and 48 are resistively heated and their temperature are controlled by adjusting the input voltage (0–15 Volts DC). The voltage controller circuitry is shown in the wiring diagram of FIG. 5. Power for these heaters is provided by a 15 Volt DC power supply (LFS-45A-15, Lambda, Melville, N.Y.)

The heated restrictors 42 and 44 terminate in collection vessel assemblies 50 and 52. These assemblies have septum seals 54 and 56 to receive the restrictors 42 and 44. Collection solvent is added to the collection solvent fingers 58 and 60, and the extraction effluent passing out of the restrictors 42 and 44 is bubbled through the collection solvent. The collection vessel assembly is discussed in greater detail below with reference to FIG. 6.

The collection solvent used in the collection vessel assembly must be an organic solvent in which the analytes are soluble and which solvent is compatible with subsequent analytical methods which are designed to detect and measure analytes. Preferred collection solvents include methylene chloride, hexane and isooctane.

Figure 2:
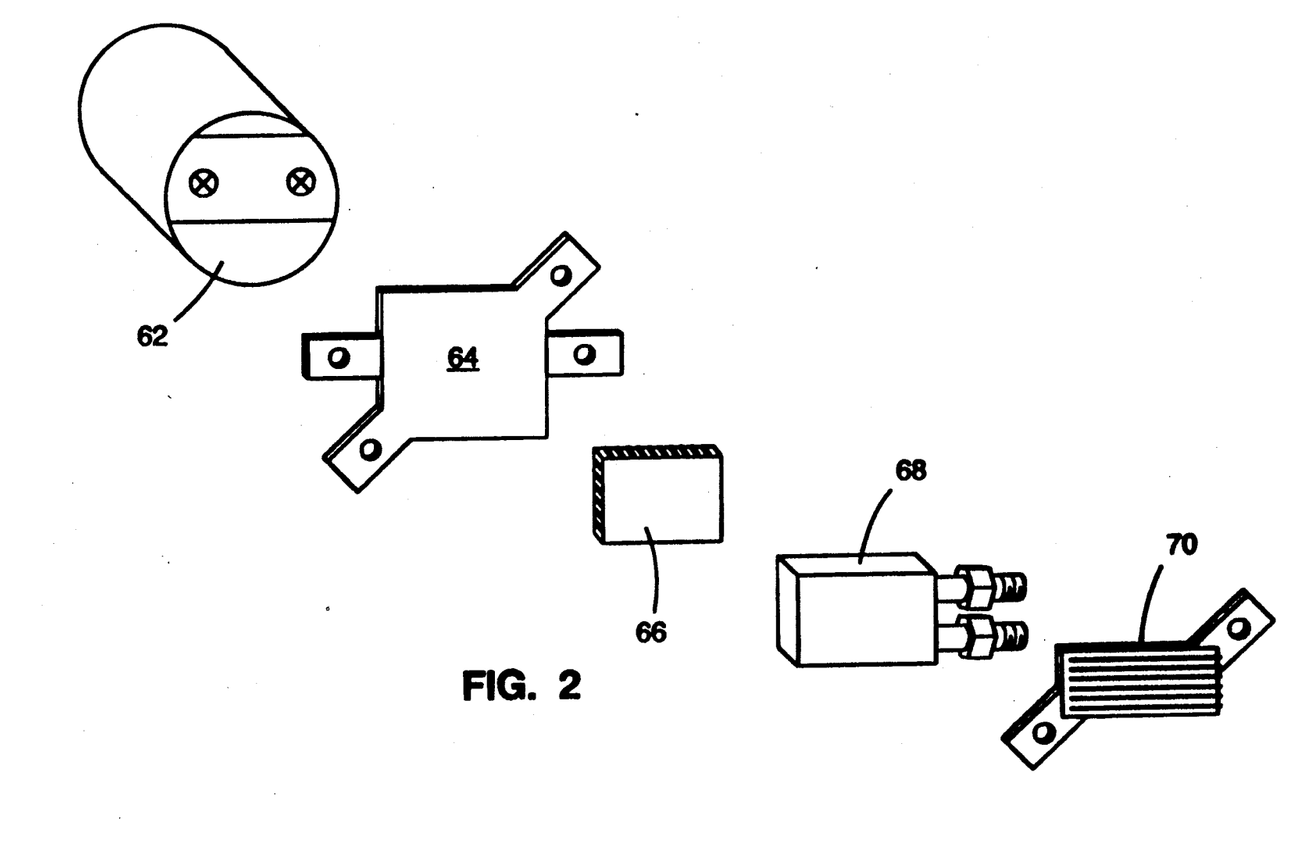
FIG. 2 is a perspective view of the pumphead cooling assembly.

A detailed view of the pumphead cooling assembly 20 is shown in FIG. 2. As described above, it is necessary to cool both the incoming flow of SFE solvent and the reciprocating pumphead 62. Our experience shows that satisfactory performance can be obtained if a temperature of 0° to 4° C. is maintained. We use single stage thermoelectric devices to provide lightweight cooling.

A 3/16" copper cooling plate 64 is attached to the pumphead 62. A thermoelectric device 66 is then sandwiched between the copper plate 64 and a liquid cooled heat exchanger 68. A small convective cooled heat sink 70 is mounted on the liquid cooled heat exchanger 68.

Figure 3:
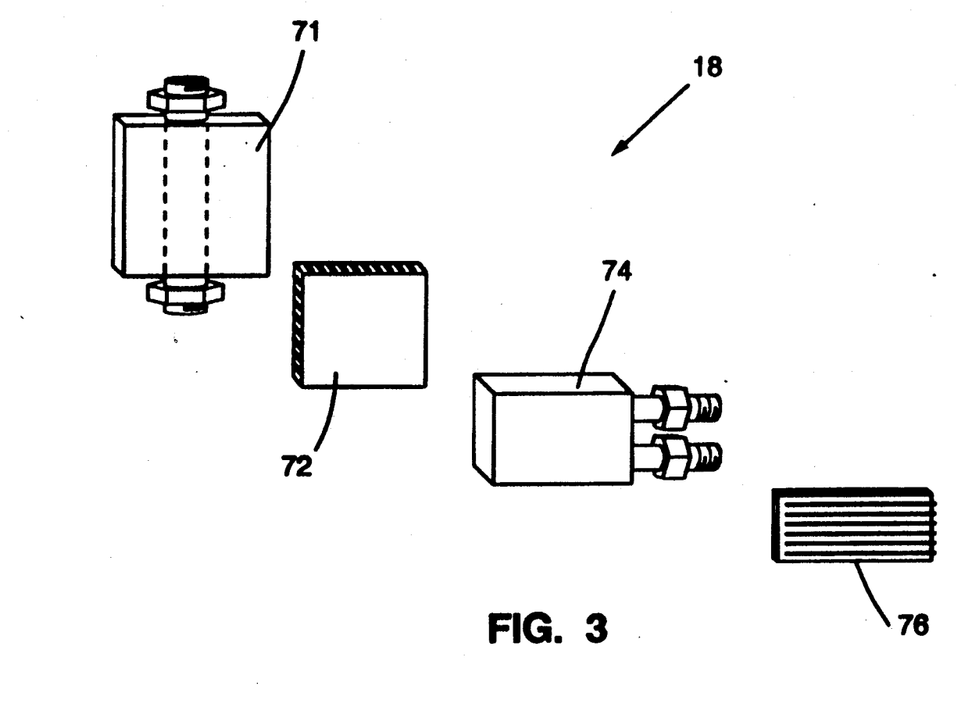
FIG. 3 is a perspective view of the SFE solvent cooling assembly.

The SFE solvent cooling assembly 18 is shown in FIG. 3. SFE solvent passes through a copper block 71 as it enters the inlet port of the pumphead. Thermoelectric device 72 is sandwiched between copper block 71 and liquid-cooled heat exchanger 74. A small heat sink 76 is placed on the liquid cooled heat exchanger 74.

Figure 4:
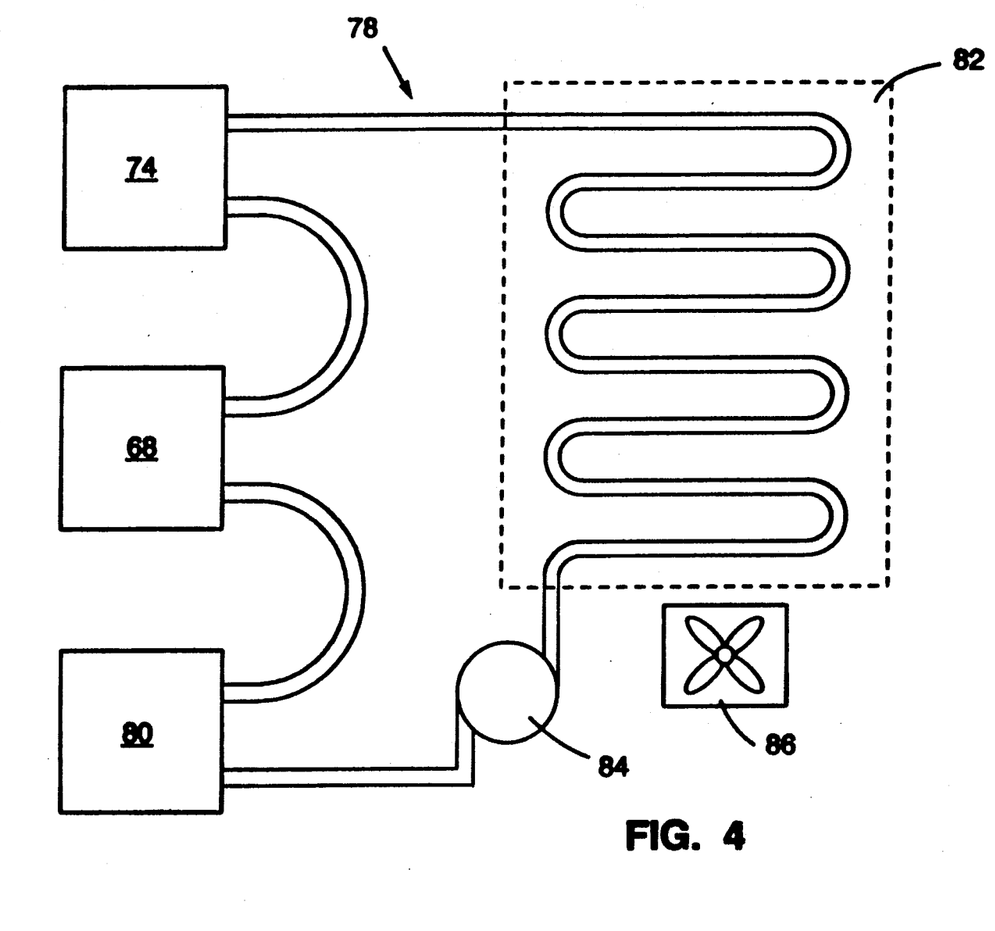
FIG. 4 is a schematic diagram of the thermoelectric cooling assembly liquid heat exchanger.

The thermoelectric devices (CP1.4-127-06L, Melcor, Trenton, NJ) provide 50 watts of cooling and require 6 amps at 15 volts DC. These thermoelectric devices are essentially solid state heat pumps and have a cold and hot side. A temperature differential of approximately 60° C. can be obtained with the devices. Therefore, in order to maintain a 0° C. cold side, the hot side must be maintained at less than 60° C. We found it necessary to incorporate a liquidcooled heat exchanger to reject the heat and to maintain an appropriate operating temperature on the hot side. The liquid flowing through the heat exchanger is a water-ethylene glycol mixture, and it is cooled by circulation through a small muffin-fan cooled radiator. This radiator system 78 is shown in FIG. 4. A maximum of 250 watts of heat must be dissipated through the combination of the closed-loop liquid system and the heat sink.

Radiator system 78 comprises the SFE solvent liquid-cooled heat exchanger 74, the pumphead liquid-cooled heat exchanger 68, and a collection flask assembly condenser 80, all connected in series. The liquid coolant is passed through radiator 82 via pump 84. A muffin fan 86 is provided to cool the radiator 82. In our present embodiment, the radiator 82 is a modified automobile air conditioner condenser radiator. Pump 84 is an aquarium pump.

Figure 5:
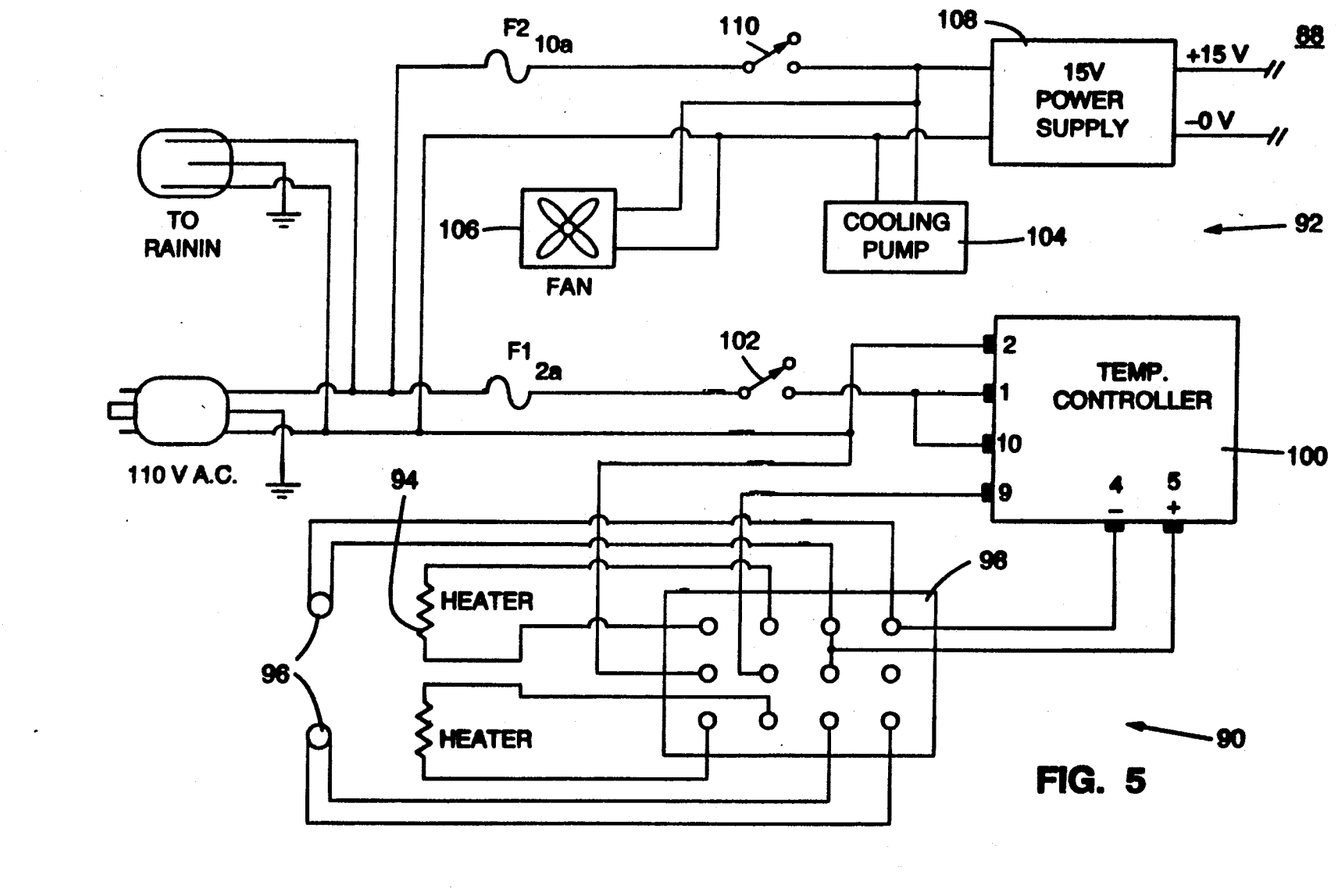
FIG. 5 is a circuit diagram for the field-portable SFE apparatus.

A circuit diagram for the preferred embodiment is presented in FIG. 5. The pump cooler switch 88 which is powered by a standard 100 v a.c. supply, includes a heater section 90 and a cooler section 92. The heater section 90 includes heater coils 94 which are driven by a pair of thermocouples 96 via a select thermocouple switch 98. The limits of the select switch 98 are set by the temperature controller 100. The temperature controller 100 is activated by a simple on/off switch 102. The cooler section 92 includes a cooling pump 104 and associated fan 106 which are rechargeable via on/off switch 110.

Figures 6, 6A, 6B:
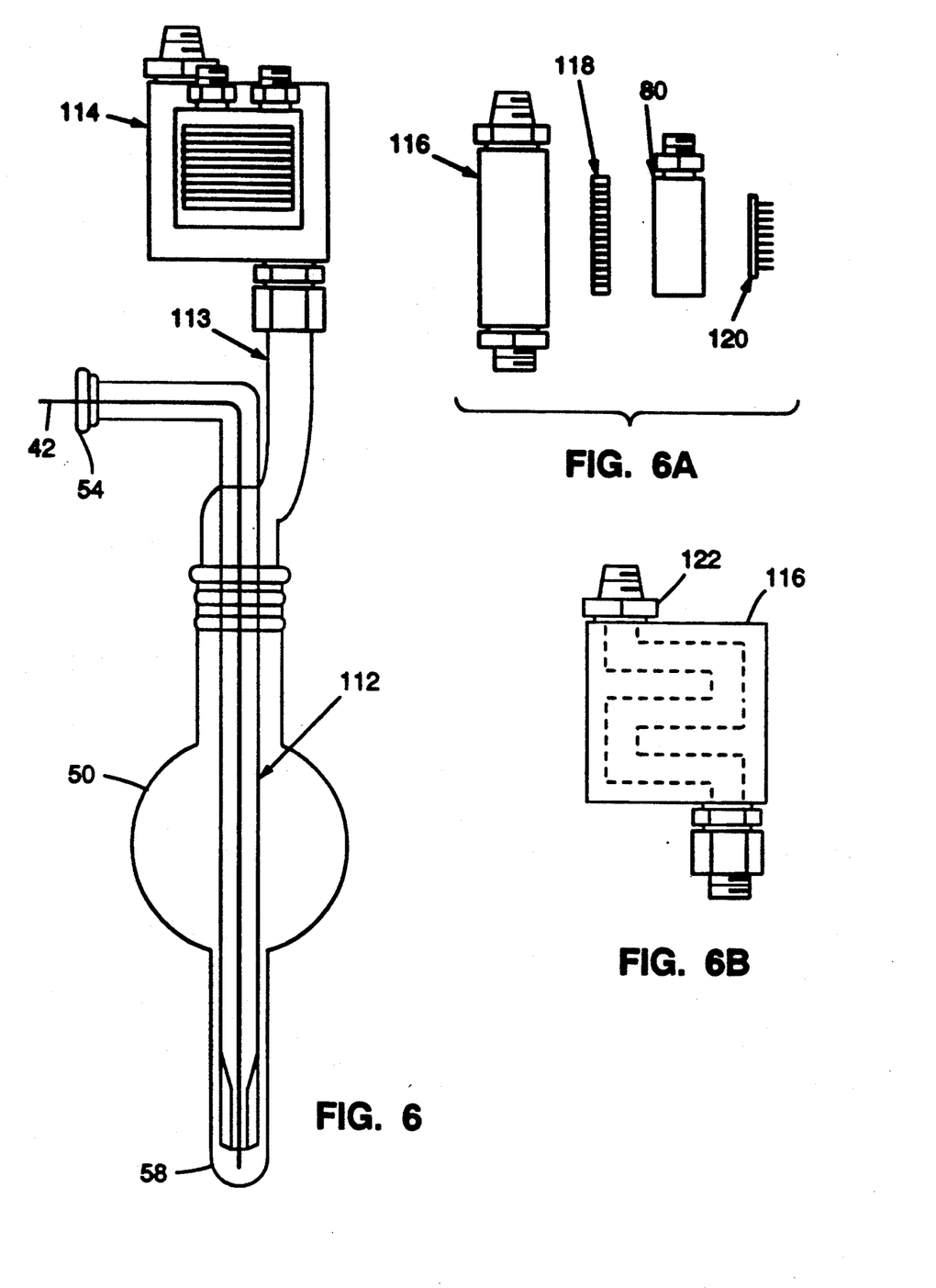

The collection vessel assembly 50 is shown in FIG. 6. The extraction effluent enters the collection flask assembly 50 through restrictor 42, passing through septum seal 54. Restrictor 42 is contained within a restrictor support tube 112 which makes a ground glass 24/40 connection with the collection vessel assembly (smog bubbler 7529, Ace Glass, Vineland, NJ). Restrictor 42 and support tube 112 terminate in the collection solvent finger 58. Collection solvent is added to the collection vessel assembly 50 to a height slightly above the bottom finger 58. This finger 58 must contain at least two inches of collection solvent for proper operation. Since it is likely that some collection solvent is evaporated during operation, the correct initial volume can be added to the collection vessel assembly 50 to provide a final volume in which the analytes are at the correct concentration level for analysis, provided that the analytes are at a sufficiently high level in the minimum solvent volume of approximately 6 mL.

We recognize that collection solvent vapors could be entrained with SFE extraction solvent. To recover these collection solvent vapors, a condenser assembly 114 is provided at the top of the collection flask assembly 50, and is shown in detail in FIG. 6a. The condenser 116 is cooled in a manner similar to that previously d(R)scribed with respect to the pumphead. The escaping vapors are passed through a copper-block cooling channel 116 to which is attached a thermoelectric cooling device 118 (CPI.0-127-05L), 35 watts cooling power requiring only 3.9 amps of power. A liquid-cooled heat exchanger 80 (attached to the radiator system described with reference to FIG. 5) is provided to dissipate heat on the hot side of the thermoelectric device 118. A' convective cooled heat sink 120 is also provided. FIG. 6b shows the path of the escaping vapors through the cooling channel 116 and out of the outlet 122.

Collection solvent loss is also minimized by the fact that the solvent is cooled below 0° C. as the SFE solvent expands at the terminus of the restrictor 42.

Working Examples

Samples. Soil samples from three manufactured gas plant sites were supplied by the Electric Power Research Institute. The plant-site samples contained coal tar, a typical waste resulting from the production of town gas. The samples homogenized as received and were not dried or sieved. Care was taken to minimize exposure to light. Samples were labeled 3-1, 3-2, 5-2, 5-3, 6-1, and 6-2. Selected samples were characterized for particle size, total organic carbon, weight loss on heating, and elemental oxide composition of the ash after heating. The results are given in Table I—III.

TABLE I

Particle Size and Total Organic Carbon Content of Soil Samples

| | anal., wt % | | | |
|---|---|---|---|---|
| sample | sand (>53 μm) | silt (2–53 μm) | clay (<2 μm) | tot. organic carbon |
| 3-2 | 51 | 36 | 13 | 5.06 |
| 5-2 | 100 | 0 | 0 | 0.35 |
| 6-1 | 87 | 5 | 8 | 19.2 |
| 6-2 | 27 | 46 | 27 | 51.3 |

TABLE II

Percent Weight Loss from Heating of Soil Samples

| sample | % loss at 105° C. (unbound H$_2$O) | % loss at 1200° C. (organic C$_1$, CO$_2$, (bound H$_2$O) | % tot. loss |
|---|---|---|---|
| 3-2 | 36.3 | 5.46 | 41.7 |
| 5-2 | 17.0 | 0.25 | 17.2 |
| 6-1 | 29.0 | 31.0 | 60.0 |
| 6-2 | 28.2 | 45.5 | 73.7 |

TABLE III

Characterization of Soil Samples by Atomic Absorption

| sample | wt % of residual ash after heating to 1200° C. | | | | | | | |
|---|---|---|---|---|---|---|---|---|
| | Na$_2$O | MgO | Al$_2$O$_3$ | SiO$_3$ | K$_2$O$^a$ | CaO | Fe$_2$O$_3$ | total |
| 3-2 | 2.66 | 0.91 | 14.7 | 74.8 | 1.90 | 1.33 | 3.02 | 100.1 |
| 5-2 | 0.28 | 0.05 | 2.95 | 92.7 | 1.10 | 0.25 | 0.36 | 97.8 |
| 6-1 | 0.69 | 1.50 | 20.9 | 55.3 | 2.20 | 5.54 | 10.5 | 99.0 |
| 6-2 | 0.54 | 2.72 | 9.71 | 32.9 | 2.10 | 43.8 | 5.08 | 100.5 |

Supercritical Fluid Extraction (SFE). Soil Samples of approximately 1 g each (weighed to within ±0.005 g) were sealed inside the stainless-steel extraction cell, which was then placed inside an oven heated to 125° C. The extraction cells were made from approximately 1-in. lengths of ¼-in. stainlesssteel tubing capped with Swagelok stainless-steel zero-volume ¼-in. to 1/16-in. column end fittings (SS-0-6-1ZV) containing 1.0-μm pore size sintered stainless-steel frits. All samples were extracted with high-purity carbon dioxide (SFC grade, Scott Specialty Gases) at pressures of 300–400 bar for 30–90 min. Flow rates ranged from 400 to 800 mL/min., with flow restrictors made out of uncoated fused silica of 50–100-μm i.d. When supercritical carbon dioxide is expanded to a gas, the volume increases by a factor of approximately $10^3$. The extraction effluent was bubbled through methylene chloride solvent and the analytes collected in a glass collection vessel. The glass collection vessel was filled with 1.0–5.0 mL of internal-standardcontaining solution to correct for final volumes and an additional approximately 20 mL of methylene chloride, after which it was wrapped in aluminum foil to minimize sample exposure to light. The inter-standard-containing solution was 50 μg/mL of 2-chloroanthracene in benzene. All solvents were distilled-in-glass, high-purity grade (American Burdick and Jackson, Muskegon, MI). A reflux condenser was connected to the collection vessel to minimize solvent losses due to evaporation. A Brinkmann Lauda RC3 recirculating water bath operated at −15° to −20° C. with a poly(ethylene glycol)/water mixture was used to cool the pump head and reflux condenser. Extracts and collection vessel washings (at least three at 1 mL each with methylene chloride) were transferred, combined, and concentrated to approximately 2 mL under a stream of high-purity nitrogen in foil-wrapped 7-mL borosilicate glass vials. Samples 5-2 and 6-2 were each extracted once, three replicates of sample 5-3 were extracted, ten replicates of sample 3-1 were extracted at 100° C., and samples 3-2 and 6-1 were each extracted successively three times.

Soxhlet Extraction. The soil samples 5-2, 5-3, and 6-2 of approximately 2 g each (weighed to within ±0.005 g) were placed inside Soxhlet extraction thimbles that had been precleaned for at least 24 h by using 200 mL each of methylene chloride. Five replicates of soil sample 3-1 (1 g each) were prepared. The samples and an empty thimble blank were the Soxhlet extracted overnight by using 200 mL of fresh methylene chloride with an approximate 1-min. cycle. The Soxhlet extraction apparatus were wrapped in aluminum foil to prevent possible sample degradation due to exposure to light. Two mL of internal-standard-containing solution was added to the 3-1 extracts to correct for final volumes. The extracts were concentrated to 1-3 mL with a rotary evaporator operated at 45° C. and were transferred to foil-wrapped vials as above. Extraction flasks were each washed at least three times with 1 mL of methylene chloride; washings were combined with the concentrated extracts. The total volume of each extract (other than the 3-1 extracts) was measured.

High Resolution Gas Chromatography (HRGC). Soxhlet and SFE extracts were analyzed by HRGC using an Hewlett-Packard (HP) 5880A gas chromatograph equipped with a 30-m×0.25-mm i.d. fused silica capillary column coated with 0.25-μm film thickness SE-54 (J & W Scientific, Folsom, CA). the capillary column was cross-linked in house by using azo-tertbutane. The oven was temperature-programmed from 40° to 280° C. at 3° C./min with 2 min isothermal at both the upper and lower temperatures. Splitless injection (0.5 min purge) was used with hydrogen as the carrier gas at 100 cm/s linear velocity. The injection port and flame ionization detector were operated at 275° and 300° C., respectively. Selected individual components were quantified according to the external standard calibration method by using 2-chloroanthracene as an internal standard as described in Wilson, B.W.; Pelroy, R.A.; Mahlum, D.D.; Frazier, M.E.; Later, D.W.; Wright, C.W., Fuel 1982, 61, 473-477. Response factors (amount/area) were calculated from standard reference polycyclic aromatic hydrocarbon (PAH) compounds chromatographed at five concentration levels ranging over 2 orders of magnitude. SFE extracts were concentrated or diluted as necessary so responses fit on the calibration curves. Known volumes of the Soxhlet extracts (other than 3-1. extracts) were diluted with known volumes of internal-standard-containing soln. prior to further concentration or dilution as necessary to insure that their responses were within the calibrated region. The response factor of a closely eluting or similar compound was used to quantify components for which standard reference compounds were not available. Components in extracts were identified by retention index, (Lee, M.L.; Vassilaros, D.L.; White, C.M.; Novotny, M. Anal. Chem. 1979, 51, 768–774. Vassilaros, D.L.; Kong, R.C.; Later, D.W.; Lee, M.L. J. Chromatoor. 1982, 252, 1–20) absolute retention times of standard reference compounds, and/or gas chromatography/mass spectrometry by using an HP 5985 quadrupole mass spectrometer operated in the electron-impact mode at 70 eV. Extracts from the ten SFE and five Soxhlet replicates were analyzed in triplicate. All other extracts were analyzed once.

SFE Recovery Study. A 1-g (weighed to within ±0.005 g) sample of a soil known to contain less than 25 ppb of individual PAH (as determined by Soxhlet extraction and analysis of extract) was placed in an SFE extraction cell. The soil was then spiked with 14 PAH standard reference compounds ranging from two to six rings in size, at levels of approximately 10 ppm (μg/g) by the addition and subsequent evaporation of 200 μL of a PAH standard solution in methylene chloride. Table IV lists the spiked compounds, their PAH standard solution concentrations, and the exact levels of each spike. The spike soil samples was then extracted as described above for 40 min at 325 bar and 100° C. using carbon dioxide; 250 μL of 2-chloroanthracene internal standard was added to the solvent in the collection vessel. The percent recoveries of each of the PAH standard reference compounds were determined by comparison of the extract's individual PAH flame ionization response relative to the internal standard to those for 200 μL of the PAH standard solution with the same amount of internal standard as was added to the SFE extract.

TABLE IV

SFE Recovery Study Results

| compound | std amt, ng/μL | spike amt[a], μg/g | & recovery |
|---|---|---|---|
| naphthalene | 56.3 | 11.3 | 40.7 |
| 2-methylnaphthalene | 50.0 | 10.0 | 52.4 |
| biphenyl | 50.7 | 10.1 | 62.5 |
| fluorene | 49.2 | 9.84 | 85.5 |
| dibenzothiophene | 49.3 | 9.86 | 91.0 |
| phenanthrene | 50.0 | 10.0 | 96.6 |
| 1-methylphenanthrene | 50.3 | 10.0 | 85.6 |
| fluoranthene | 49.7 | 9.94 | 85.1 |
| pyrene | 49.0 | 9.80 | 89.7 |
| benzo[b]fluorene | 49.8 | 9.96 | 99.4 |
| chrysene | 50.1 | 10.0 | 96.0 |
| benzo[e]pyrene | 66.0 | 13.2 | 120 |
| indeno[1,2,3-cd]pyrene | 19.9 | 3.98 | 119 |
| benzo[ghi]perylene | 49.6 | 9.93 | 124 |

[a]Based on a 200-μL spike of the standard onto 1.00 g of soil.

Linear responses were assumed. HRGC conditions were as described previously except the oven was temperature programmed at 4° C./min.

TABLE V

Identification of Components in Soil Sample 6-2 Supercritical Fluid Extract

| peak no.[a] | mol wt | compound |
|---|---|---|
| 1 | 116 | indene |
| 2 | 130 | methylindenes |
| 3 | 128 | naphthalene |
| 4 | 134 | benzo[b]thiophene |
| 5 | 142 | 2-methylnaphthalene |
| 6 | 142 | 1-methylnaphthalene |

TABLE V-continued

Identification of Components in Soil Sample 6-2 Supercritical Fluid Extract

| peak no.[a] | mol wt | compound |
|---|---|---|
| 7 | 154 | biphenyl |
| 8 | 156 | dimethylnaphthalenes |
| 9 | 152 | acenaphthylene |
| 10 | 154 | acenaphthene |
| 11 | 168 | dibenzofuran |
| 12 | 166 | fluorene |
| 13 | 182 | methylfluorenes, |
| 14 | 184 | dibenzothiophene |
| 15 | 178 | phenanthrene |
| 16 | 178 | anthracene |
| 17 | 167 | carbazole |
| 18 | 192 | 3-methylphenanthrene |
| 19 | 192 | methylphenanthrene |
| 20 | 190 | 4H-cyclopental[def]phenanthrene |
| 21 | 192 | 4- and 9-methylphenanthrene |
| 22 | 192 | 1-methylphenanthrene |
| 23 | 202 | fluoranthene |
| 24 | 202 | acephenanthrylene |
| 25 | 202 | pyrene |
| 26 | 216 | benzo[a]fluorene |
| 27 | 216 | benzo[b]fluorene, methylpyrene |
| 28 | 216 | methylprenes |
| 29 | 234 | benzo[b]naphthol[1,2-d]thiophene |
| 30 | 228 | benz[a]anthracene |
| 31 | 228 | chrysene, triphenylene |
| 32 | 252 | benzofluoranthenes |
| 33 | 252 | benzo[e]pyrene |
| 34 | 252 | benzo[a]pyrene |
| 35 | 252 | perylene |
| 36 | 276 | indeno[1,2,3-cd]pyrene |
| 37 | 276 | benzo[ghi]perylene |
| 38 | 302 | naphthofluorenathenes/pyrenes |

Figure 7:
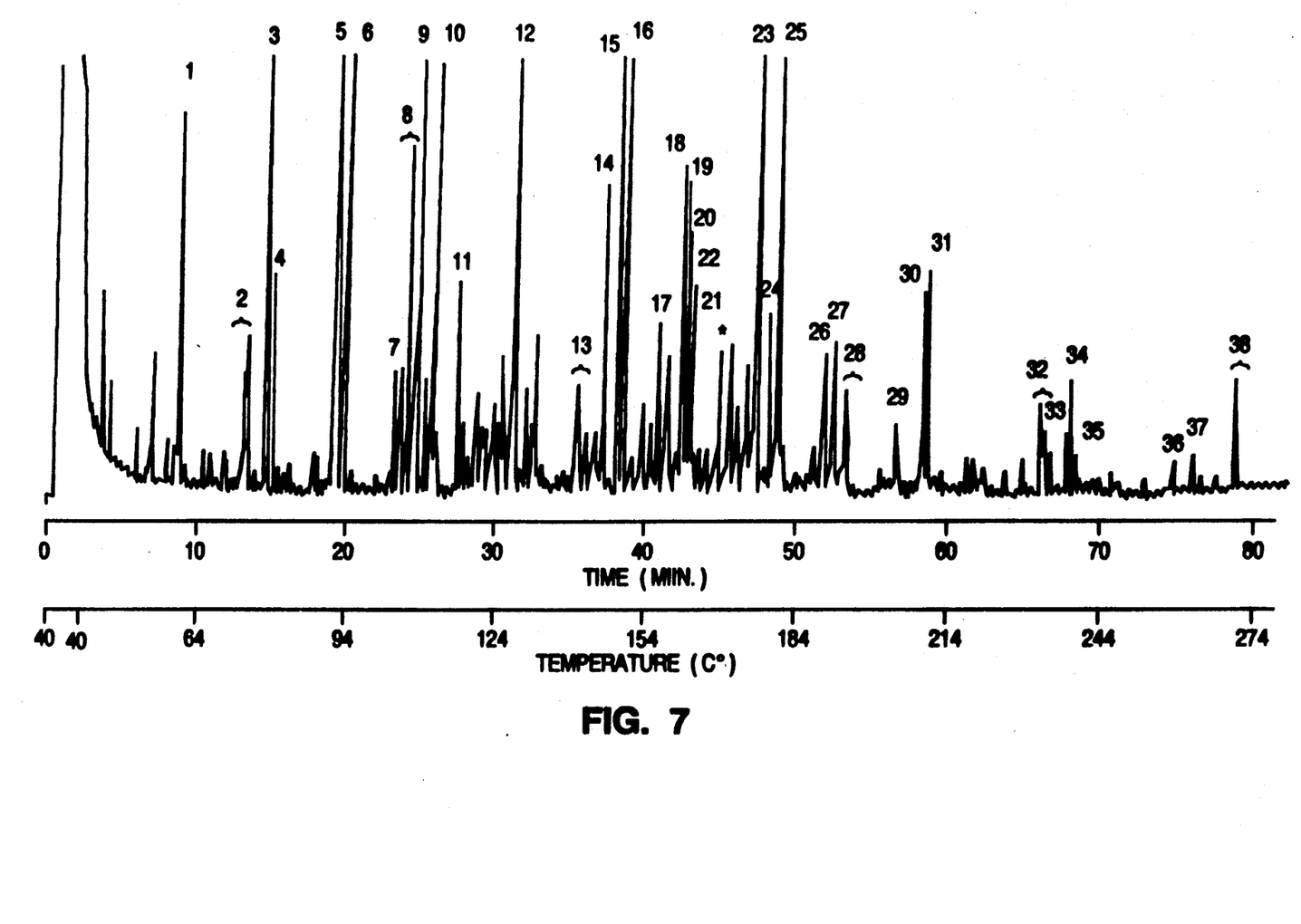
FIG. 7 is a high resolution gas chromatogram of the SFE extract from manufactured gas waste site sample 6-2.

[a]Numbers refer to peaks labeled in FIG. 7.

compounds spiked onto a soil sample at approximately a 10 ppm level ranged from 44% to 124%, with only the most volatile lower molecular weight PAH compounds giving less than quantitative recoveries (<80%). It is likely that the most significant losses of these volatile compounds occurred during spiking rather than extraction and analysis. The average recovery for all the spiked PAH compounds ranging from two to six rings in size was 90%, quantitative results within experimental error. Similar results (95% average recovery) were obtained at spiking levels ranging from 0.8 to 5 ppm by using SRM 1647 (PAH priority pollutants standard reference material; National Bureau of Standards).

The high-resolution gas chromatogram of the SFE extract from soil sample 6-2 is shown in FIG. 7. The profile of chemical components from this sample corresponds to the profile of chemical components typically observed in coal tar. (Wise, S.A.; Benner, B.A.; Byrd, G.D.; Chesler, S.N.; Rebbert, R.E.; Schantz, M.M. *Anal Chem.* 1988, 60, 887–894.) The major components of the sample's gas chromatographable portion are identified in Table V; they ranged from two-ringed polycyclic aromatic compounds (PAC) to six-ringed PAC with their alkylated homologues. All of the extracts from the five soil samples gave chemical component profiles similar to that shown in FIG. 7 except that the concentration levels of the individual components differed depending upon the sample.

The concentration of selected PAH in SFE and Soxhlet extracts of soil samples 5-3, 5-2, 6-2, and 3-1 are given in Table VI. Sample 5-2 had low levels of PAH, samples 5-3 and 3-1 had medium levels of PAH, and sample 6-2 had high levels of PAH relative to each other. Additional compounds believed to be contaminants were present in the Soxhlet extracts (as determined from the chromatogram of the Soxhlet thimble blank) compared to SFE extracts.

TABLE VI

Concentrations of Selected Polycyclic Aromatic Hydrocarbon Compounds in Manufactured Gas Waste Site Samples As Determined by Gas Chromatographic Analysis of Supercritical Fluid and Soxhlet Extracts

| | concn in manufactured gas waste site samples[a], ppm (g/g) | | | | | | | |
|---|---|---|---|---|---|---|---|---|
| compound | SFE 5-2 | Soxhlet 5-2 | SFE 5-3 (N = 3) | Soxhlet 5-3 | SFE 6-2 | Soxhlet 6-2 | SFE 3-1 (N = 10) | Soxhlet 3-1 (N = 5) |
| naphthalene | 0.09 | 0.09 | 6.5 ± 2.6 | 6.3 | 2140 | 2540 | | |
| 1-methylnaphthalene | 0.05 | | 5.7 ± 1.9 | 5.0 | 1510 | 1660 | | |
| 2-methylnaphthalene | 0.16 | 0.51 | 4.1 ± 1.3 | 3.4 | 1170 | 1280 | | |
| biphenyl | | 0.08 | 1.1 ± 0.3 | 0.94 | 173 | 149 | | |
| acenaphthylene | | 0.04 | 3.3 ± 0.9 | 2.7 | 783 | 741 | | |
| acenaphthene | | 0.11 | 3.8 ± 0.9 | 4.1 | 813 | 815 | | |
| fluorene | 0.08 | 0.10 | 4.4 ± 0.6 | 4.2 | 780 | 830 | 20.1 ± 2.2 | 20.4 ± 1.1 |
| dibenzothiophene | 0.53 | 0.03 | 2.3 ± 0.4 | 1.6 | 637 | 656 | 13.3 ± 4.1 | 11.3 ± 2.4 |
| phenanthrene | 7.8 | 0.25 | 17 ± 2 | 15 | 2330 | 2280 | 45.7 ± 5.4 | 41.7 ± 1.4 |
| anthracene | | 0.27[b] | 6.2 ± 1.6 | 5.0[b] | 550 | 638[b] | | |
| carbazole | | | | | | | 49.1 ± 4.6 | 47.3 ± 1.3 |
| 3-methylphenanthrene | | 0.06 | 3.1 ± 0.4 | 2.6 | 614 | 555 | 47.7 ± 4.8 | 43.1 ± 0.5 |
| 2-methylphenanthrene | 0.12 | 0.24 | 2.6 ± 0.4 | 2.5 | 326 | 435 | 41.2 ± 2.7[e] | 38.1 ± 0.6 |
| 9- or 4-methylphenanthrene | | | | | | | 57.2 ± 3.1 | 54.6 ± 1.6 |
| 1-methylphenanthrene | | | | | | | 42.2 ± 3.0 | 39.6 ± 0.1 |
| fluoranthene | 0.31 | 0.52 | 8.5 ± 1.4 | 6.8 | 825 | 1100 | 48.1 ± 3.0 | 48.8 ± 1.7 |
| pyrene | 0.47 | 0.83 | 11 ± 2 | 11 | 825 | 1350 | 57.0 ± 3.7 | 59.2 ± 4.4 |
| benzo[b]fluorene | | 0.21 | 4.0 ± 1.3 | 28[e] | 563 | 468 | | |
| benz[a]anthracene | 0.55 | 2.3[b] | 4.6 ± 1.6 | 9.4[b] | 529 | 493[b] | 30.5 ± 2.6[e] | 36.7 ± 1.5 |
| chrysene | | 0.30 | 3.5 ± 0.9 | 3.3 | 468 | 544 | 40.7 ± 3.2[e] | 49.6 ± 1.9 |
| benzo[e]pyrene | 0.29 | 0.44 | 1.7 ± 0.6 | 2.6 | 225 | 242 | 11.9 ± 1.1[e] | 15.3 ± 1.2 |
| benzo[a]pyrene | | 0.32 | 3.0 ± 1.0 | 3.8 | 473 | 475 | 21.1 ± 4.2 | |
| indeno[1,2,3-cd]pyrene | 0.18 | 0.14 | 1.3 ± 0.5 | d | 225 | | | |
| benzol[ghi]perylene | 0.10 | 0.23 | 1.0 ± 0.2 | d | 297 | | | |

[a]No data given when none detected or not analyzed.
[b]Contaminant in Soxhlet thimble blank.
[d]Data showed significant difference (0.05) from Soxhlet.
[e]Contaminant appeared to be present in sample.

Results

The results from the SFE recovery study are given in Table IV. Recoveries of the 14 PAH standard reference The greatest amount of variation between the Soxhlet and SFE data was present in the lowest level sample, 5-2. Many components were detected in the Soxhlet extract that were below the detection limits in the SFE extract. It appeared that the minimum detectable limit of the SFE method as applied was about 50–100 ppb. No particular efforts were made to go below this detection limit during the SFE methods development, although by doubling the sample extraction weight (as was the Soxhlet extract) and concentrating the extract volume further, a minimum detectable limit of about 10–25 ppb could be easily achieved. Given the same sample size, the detection limits achievable by SFE is essentially the same as Soxhlet extraction.

An indication of the reproducibility of the SFE method is given by the three early replicate SFE analyses of sample 5-3 in Table VI. The standard deviations of the mean averaged ±25% of the mean, with some values as low as ±10% of the mean. As the SFE method was refined and became more routine, the reproducibility of the extracts were expected to improve. This indeed was the case as the results from a more complete study of reproducibility indicate (data for sample 3-1 in Table VI). Sample 3-1 had an increased amount of alkylated PAH relative to parent PAH than did any of the other soil samples. This led to an even more complex chromatogram than that shown in FIG. 7. Ten replicate SFE extractions were performed. The SFE extract results averaged ±10% difference from the Soxhlet extract results. Of the 14 compounds quantified in the SFE and Soxhlet extracts, there were only four compounds that showed significantly different concentrations (at 95% confidence limits). Three of the four compounds were the highest molecular weight compounds quantified (noted in Table VI). The average coefficient of variation for all 14 compounds (CV; percent standard deviation) was 16 for the SFE and 11 for the Soxhlet extraction. A nested analysis of variance showed the average CV from the SFE replication was 4 with an average CV from the analysis of 12; the average CV from the Soxhlet extraction replication was 1 with an average CV of 10 from the analysis.

The concentration of selected PAH determined from the SFE extracts of manufactured gas waste site samples 5-3 and 6-2 were comparable to the concentrations of the same components determined from the Soxhlet extracts. The SFE extract results averaged a ±12% difference from the Soxhlet extract results for sample 6-2. The SFE extract results averaged a ±20% difference from the Soxhlet extract results for sample 5-3 (not including the Soxhlet data that was questionable due to contaminants in the thimble blank). In addition, roughly two-thirds of the concentrations determined from the Soxhlet extract were within one standard deviation of the mean of the SFE extract data for sample 5-3; 94% were within two standard deviations of the mean (not including the questionable Soxlet data.)

TABLE VII

Concentrations of Selected Polycyclic Aromatic Hydrocarbon Compounds in Manufactured Gas Waste Site Samples As Determined by Gas Chromatographic Analysis of Successive Supercritical Fluid Extracts

| combined | ppm of combined SFE 3-2[b] | % SFE I | 3-2 % SFE II | % SFE III | ppm of combined SFE 6-1[b] | % SFE I | 6-1 % SFE II | % SFE III |
|---|---|---|---|---|---|---|---|---|
| naphthalene | 8.2 | 100 | 0 | 0 | 42 | 87 | 9 | 4 |
| 1-methylnaphthalene | 14 | 100 | 0 | 0 | 8.1 | 100 | 0 | 0 |
| 2-methylnaphthalene | 11 | 100 | 0 | 0 | 4.2 | 100 | 0 | 0 |
| biphenyl | 0.86 | 100 | 0 | 0 | 1.5 | 100 | 0 | 0 |
| acenaphthylene | 7.6 | 100 | 0 | 0 | 3.0 | 83 | 0 | 17 |
| acenaphthene | 0.37 | 100 | 0 | 0 | 7.1 | 61 | 24 | 15 |
| fluorene | 2.0 | 100 | 0 | 0 | 3.6 | 100 | 0 | 0 |
| dibenzothiophene | 1.0 | 100 | 0 | 0 | 5.4 | 100 | 0 | 0 |
| phenanthrene | 14 | 100 | 0 | 0 | 51 | 91 | 7 | 2 |
| 3-methylphenanthrene | 4.4 | 100 | 0 | 0 | 17 | 84 | 12 | 5 |
| 2-methylphenanthrene | 4.5 | 100 | 0 | 0 | 18 | 81 | 13 | 6 |
| fluoranthene | 3.5 | 100 | 0 | 0 | 110 | 84 | 14 | 2 |
| pyrene | 4.0 | 100 | 0 | 0 | 180 | 78 | 19 | 3 |
| benzo[b]fluorene | 1.1 | 100 | 0 | 0 | 80 | 78 | 19 | 3 |
| benz[a]anthracene | 1.3 | 100 | 0 | 0 | 135 | 80 | 17 | 3 |
| chrysene | 1.2 | 100 | 0 | 0 | 155 | 76 | 20 | 4 |
| benzo[e]pyrene | 0.18 | 100 | 0 | 0 | 150 | 62 | 29 | 9 |
| benzo[a]pyrene | 0.29 | 100 | 0 | 0 | 180 | 66 | 27 | 7 |
| indeno[1,2,3-cd]pyrene | 2.4 | 100 | 0 | 0 | 130 | 57 | 30 | 13 |
| benzol[ghi]perylene | 0.17 | 100 | 0 | 0 | 140 | 43 | 36 | 21 |

*Samples were each extracted three times in succession.
[b] g/g.

The two highest molecular weight compounds, the indeno[1.2.3-cd]pyrene and the benzo[ghi]-perylene, showed the greatest deviation between the two extraction methods, with the SFE extract only having an extraction efficiency of about half that of the Soxhlet extraction. This was probably due to the lower solubility of the higher molecular weight compounds in the supercritical carbon dioxide. The SFE method employed during these investigations used a very rapid (30 min) extraction, and the extraction time and/or fluid flow rate may need to be increased to achieve a better extraction efficiency of the heavier molecular weight species.

The concentrations of selected PAH determined from three successive SFE extracts for manufactured gas waste site samples 3-2 and 6-1 are given in Table VII. The results from the three successive extractions were combined together to get a total amount of individual PAH compounds in each of the samples. The percent extracted in each successive extraction was then calculated from the total. Sample 3-2 had low levels of high molecular weight species, whereas sample 6-1 had high levels of the same species, relative to each other. The first 30 min SFE of sample 3-2 removed 100% of the PAH detected in it; no additional significant concentrations were detected in the second and third successive SFE extracts. The first 30-min SFE of sample 6-1 removed a little over an average of 80% of the PAH detected in it; the second 30-min SFE removed about 14% of the total, and the third 30-min SFE removed about 6% of the total. The percent of the total concentration of the individual PAH in the first SFE tended to decrease with molecular weight increase. Correspondingly, the percent of the total concentration of the individual PAH in the second and third SFE tended to increase with molecular weight increase. This result again shows the effects of the decreasing solubility of high molecular weight species in the supercritical carbon dioxide. For samples with low levels of such species (less than about 50 ppm), a 30-min SFE appears to be adequate; however, increased extraction time and/or increased fluid flow rate may be necessary for samples with high levels of high molecular weight species. Since solvation of the high molecular weight compounds is related to the pressure of extraction, (Czubryt, J.J.; Myers, M.N.; Gidding, J.C., *J. Phys. Chem.*, 1970, 74, 4260-4266) higher pressures may increase the solubility of these compounds, as would the addition of a solvent modifier, such as methanol.

Discussion

Analyses of these six manufactured gas site soil samples shows the wide variability in coal tar contamination from different locations. Individual PAH concentrations in the soil samples ranged over 5 orders of magnitude. The soil samples in approximate order of greatest coal tar contamination to least contamination were 6-2>6-1>3-1>5-3, 3-2>5-2. Although these samples were randomly chosen and were from independent sites, it appeared that the soils with higher clay contents (Table I) and lower sand and silt tended to contain higher concentrations of coal tar. Due to limited data available about the soil samples, it is not known if the PAH concentration ranges were due to soil type or sample location relative to the source of contamination, or both.

The detection limits of the SFE method as applied were in the 50-100 ppb for PAH compounds. These low detection limits allow the SFE method (with subsequent gas chromatographic analysis) to be applicable to solid environmental samples such as soils and sediments. The reproducibility of the method (including sampling and analysis) during the development of SFE for the manufactured waste gas site samples was reasonable (± approximately 25% standard deviation from the mean for three early determinations; ±16% for ten later determinations). The greatest amount of variability of the method was the gas chromatographic analysis (CV of 12) due to the highly complex extract mixture and the limits of current electronic integration of chromatographic peaks. This study showed similar reproducibility (i.e., of the same order of magnitude) is possible with the SFE method compared to the more traditional Soxhlet extraction.

The PAH extraction efficiencies of the SFE were comparable to those of Soxhlet extraction when the concentrations of the PAH compounds in the manufactured gas waste site samples were in partes per million. The only exception was the higher molecular weight compounds tended to have lower extraction efficiencies in the 30-min SFE versus the overnight Soxhlet than about 50 ppm each of higher molecular weight PAH or if those compounds are of particular interest, an SFE time of greater than 30 min or increased flow rates over the same amount of time would be necessary under the conditions used. Both options would be practical. No attempts were made to fractionate the samples by controlling the solvating power of the supercritical carbon dioxide in this study, although this potential does exist.

We claim:

1. A combination for use in portable supercritical fluid extraction of analytes of semivolatile and higher molecular weight materials from a solid absorbent matrix comprising:
   a) reciprocating high pressure liquid chromatography pump having a pumphead having pumphead cooling means;
   b) pumphead cooling means comprising a copper plate mounted on said pumphead, said copper plate attached to a thermoelectric cooler assembly;
   c) including a wafer-shaped, single stage thermoelectric cooler, a liquid cooled copper heat exchanger, and a convective cooled heat sink a heated extraction effluent restriction tube; and,
   d) a collection flask assembly which is designed to sealingly receive said extraction effluent restriction tube, said collection flask assembly having a collection tube for holding collection solvent, and having a collection solvent condenser provided at the top of the collection flask assembly to condense collection solvent vapors entrained by escaping Supercritical Fluid Extraction solvent and wherein said combination is sized and dimensioned for field use.

* * * * *